(12) United States Patent
Tichy et al.

(10) Patent No.: US 7,504,369 B2
(45) Date of Patent: Mar. 17, 2009

(54) METHODS AND COMPOSITIONS FOR DECONTAMINATING SURFACES EXPOSED TO CHEMICAL AND/OR BIOLOGICAL WARFARE COMPOUNDS

(75) Inventors: Daryl J. Tichy, Orem, UT (US); Brian G. Larson, Alpine, UT (US)

(73) Assignee: Solutions BioMed, LLC, Orem, UT (US)

( * ) Notice: Subject to any disclaimer, the term of this patent is extended or adjusted under 35 U.S.C. 154(b) by 119 days.

(21) Appl. No.: 11/510,133

(22) Filed: Aug. 24, 2006

(65) Prior Publication Data

US 2007/0048175 A1 Mar. 1, 2007

Related U.S. Application Data

(63) Continuation-in-part of application No. 11/361,836, filed on Feb. 24, 2006, and a continuation-in-part of application No. 11/361,841, filed on Feb. 24, 2006, and a continuation-in-part of application No. 11/361,837, filed on Feb. 24, 2006, and a continuation-in-part of application No. 11/361,665, filed on Feb. 24, 2006, now Pat. No. 7,351,684.

(60) Provisional application No. 60/656,723, filed on Feb. 25, 2005.

(51) Int. Cl.
*C11D 7/18* (2006.01)
*C11D 3/48* (2006.01)

(52) U.S. Cl. .............. 510/110; 510/161; 510/199; 510/235; 510/238; 510/319; 510/302; 510/309; 510/362; 510/367; 510/370; 510/372; 510/375; 510/382

(58) Field of Classification Search ........... 510/110, 510/372, 161, 199, 235, 238, 302, 309, 319, 510/362, 370, 367, 375, 382
See application file for complete search history.

(56) References Cited

U.S. PATENT DOCUMENTS

| | | | |
|---|---|---|---|
| 716,077 A | 12/1902 | Morrin | |
| 734,467 A | 7/1903 | Martien | |
| 2,103,999 A | 12/1937 | Muller et al. | |
| 2,304,104 A | 12/1942 | Klabunde et al. | |
| 4,021,338 A | 5/1977 | Harkin | |
| 4,297,298 A | 10/1981 | Crommelynch et al. | |
| 4,311,598 A * | 1/1982 | Verachtert | 210/757 |
| 4,321,255 A | 3/1982 | Boden | |
| 4,414,127 A * | 11/1983 | Fu | 510/115 |
| 4,655,975 A | 4/1987 | Snoble | |
| 4,826,658 A | 5/1989 | Kay | |
| 4,915,955 A * | 4/1990 | Gomori | 424/616 |
| 5,349,083 A | 9/1994 | Brougham et al. | |
| 5,357,636 A * | 10/1994 | Dresdner et al. | 2/161.7 |
| 5,368,867 A | 11/1994 | Da Silva et al. | |
| 5,419,908 A | 5/1995 | Richter et al. | |
| 5,437,858 A | 8/1995 | Hungerbach et al. | |
| 5,508,046 A | 4/1996 | Cosentino et al. | |
| 5,563,132 A | 10/1996 | Bodaness | |
| 5,709,870 A | 1/1998 | Yoshimura et al. | |
| 5,824,267 A | 10/1998 | Kawasumi et al. | |
| 5,945,032 A * | 8/1999 | Breitenbach et al. | 252/186.29 |
| 5,951,993 A * | 9/1999 | Scholz et al. | 424/405 |
| 5,977,403 A | 11/1999 | Byers | |
| 5,997,585 A | 12/1999 | Scialla et al. | |
| 6,027,469 A | 2/2000 | Johnson | |
| 6,114,298 A | 9/2000 | Petri et al. | |
| 6,197,814 B1 | 3/2001 | Arata | |
| 6,200,946 B1 | 3/2001 | Blum et al. | |
| 6,218,351 B1 | 4/2001 | Busch et al. | |
| 6,231,848 B1 * | 5/2001 | Breitenbach et al. | 424/78.24 |
| 6,242,009 B1 * | 6/2001 | Batarseh et al. | 424/618 |
| 6,257,253 B1 | 7/2001 | Lentsch et al. | |
| 6,277,414 B1 * | 8/2001 | Elhaik et al. | 424/616 |
| 6,302,968 B1 | 10/2001 | Baum et al. | |

(Continued)

FOREIGN PATENT DOCUMENTS

GB 2189394 * 10/1987

(Continued)

OTHER PUBLICATIONS http://web.archive.org/web/20060217191603/http://sanosilbiotech.com/start_food.html.*

(Continued)

*Primary Examiner*—Charles I Boyer
(74) *Attorney, Agent, or Firm*—Thorpe North & Western LLP

(57) ABSTRACT

The present invention is drawn to methods and compositions for use in partially or fully decontaminating surfaces which have been contaminated with chemical or biological warfare agents. The invention includes contacting the contaminated surface with a composition capable of ameliorating the negative effects caused by the warfare agent. In one embodiment, the composition includes an aqueous vehicle of water and from 0.001 wt % to 40.0 wt % of a peroxygen. Additionally, the composition can include from 0.001 ppm to 50,000 ppm by weight of a transition metal based on the aqueous vehicle content. Optionally, an alcohol can be included in the composition. In one embodiment, the transition metal can be in the form of a colloidal transition metal, such as colloidal silver.

43 Claims, No Drawings

U.S. PATENT DOCUMENTS

| | | |
|---|---|---|
| 6,306,812 B1 | 10/2001 | Perkins et al. |
| 6,368,611 B1 | 4/2002 | Whitbourne et al. |
| 6,379,712 B1 | 4/2002 | Yan et al. |
| 6,436,342 B1 | 8/2002 | Petri et al. |
| 6,540,791 B1* | 4/2003 | Dias .............................. 8/111 |
| 6,569,353 B1* | 5/2003 | Giletto et al. .......... 252/186.28 |
| 6,583,176 B2 | 6/2003 | Arata |
| 6,630,172 B2 | 10/2003 | Batarseh |
| 6,660,289 B1* | 12/2003 | Wilmotte et al. ............. 424/405 |
| 6,743,348 B2 | 6/2004 | Holladay et al. |
| 6,797,302 B1 | 9/2004 | Ben Yehuda et al. |
| 6,827,766 B2 | 12/2004 | Carnes et al. |
| 6,939,564 B2 | 9/2005 | Ranger et al. |
| 6,939,566 B2 | 9/2005 | Batarseh et al. |
| 6,962,714 B2 | 11/2005 | Hei et al. |
| 7,033,511 B2* | 4/2006 | Zawada et al. .............. 210/764 |
| 2002/0137648 A1 | 9/2002 | Sharma et al. |
| 2003/0008797 A1 | 1/2003 | Hage et al. |
| 2003/0099717 A1* | 5/2003 | Cabrera ...................... 424/616 |
| 2003/0235623 A1* | 12/2003 | Van Oosterom ............. 424/616 |
| 2004/0067159 A1 | 4/2004 | Carnes et al. |
| 2004/0170742 A1* | 9/2004 | Ben Yehuda et al. ........ 426/615 |
| 2004/0234569 A1 | 11/2004 | Nakada et al. |
| 2005/0013836 A1 | 1/2005 | Raad |
| 2005/0194357 A1 | 9/2005 | Liu et al. |
| 2005/0256017 A1 | 11/2005 | Dykstra |
| 2005/0256200 A1 | 11/2005 | Burkhart et al. |
| 2006/0035808 A1 | 2/2006 | Ahmed et al. |
| 2006/0122082 A1 | 6/2006 | Paul |
| 2006/0182813 A1 | 8/2006 | Holladay |
| 2006/0198798 A1 | 9/2006 | Tichy et al. |
| 2006/0198876 A1 | 9/2006 | Tichy et al. |
| 2006/0199752 A1 | 9/2006 | Tichy et al. |
| 2006/0240381 A1* | 10/2006 | Rizoiu et al. ................... 433/80 |
| 2006/0263239 A1 | 11/2006 | Tichy et al. |
| 2007/0053850 A1 | 3/2007 | Tichy et al. |
| 2007/0059202 A1 | 3/2007 | Tichy et al. |
| 2007/0059255 A1 | 3/2007 | Tichy et al. |
| 2007/0254044 A1* | 11/2007 | Karandikar et al. ......... 424/618 |
| 2008/0000931 A1 | 1/2008 | Tichy et al. |

FOREIGN PATENT DOCUMENTS

| | | |
|---|---|---|
| WO | WO 03/080231 | 10/2003 |
| WO | WO 2005/000324 | 1/2005 |
| WO | WO 2006/079109 | 7/2006 |

OTHER PUBLICATIONS

The interaction of silver ions and hydrogen peroxide in the inactivation of *E coli*: a preliminary evaluation of a new long lasting residual drinking water disinfectant; Water Science and Technology vol. 31 No. 5-6 pp. 123-129 (1995).*

U.S. Appl. No. 11/891,316; Tichy et al. filed Aug. 8, 2007.

Schuster, A. et al., "Persistent silver disinfectant for the environment: Myth and reality," Am. J. Infect. Control, Jun. 2003, pp. 309-311, vol. 32.

Brady, Michael J. et al., "Persistent silver disinfectant for the environmental control of pathogenic bacteria," Am. J. Infect. Control, Aug. 2004, pp. 208-214, vol. 31 (4).

Brentano, Loreno et al., "Antibacterial efficacy of a colloidal silver complex," Surg. Forum, 1966, pp. 76-78, vol. 17.

Phillips, Charles R., et al., "Chemical Disinfectant," Annual Review of Microbiology, Oct. 1958, pp. 525-550, vol. 12.

Monarca, S. et al, "Decontamination of dental unit waterlines using disinfectants and filters," Abstract Only, Minerva Stomatol., Oct. 2002, vol. 10.

Yin, Huiyong, "Analysis of Diacyl Peroxides by Ag+ Coordination Ionspray Tandem Mass Spectrometry: Free Radical Pathways of Complex Decomposition," J. Am. Soc. Mass Spectrum, Apr. 2001, pp. 449-455, vol. 12 (4).

Surdeau, N. et al, Sensitivity of bacterial viofilms and planktonic cells to a new antimicrobial agent, Oxsil 320N, Journal of Hospital Infection 2006, 62, 487-493, www.elsevierhealth.com/journals/jhin.

http://web.archive.org/web/20060217191603/http://sanosilbiotech.com/start_food.html, Virosil F&B, "Swift Virucidal with Swiss Precision," Feb. 17, 2006, 5 pages.

* cited by examiner

METHODS AND COMPOSITIONS FOR DECONTAMINATING SURFACES EXPOSED TO CHEMICAL AND/OR BIOLOGICAL WARFARE COMPOUNDS

The present application is a continuation-in-part of U.S. patent application Ser. Nos. 11/361,836; 11/361,841; 11/361,837; and 11/361,665 now U.S. Pat. No. 7,351,684, each of which was filed on Feb. 24, 2006, and each of which claims the benefit of U.S. Provisional Patent Application No. 60/656,723, filed on Feb. 25, 2005.

FIELD OF THE INVENTION

The present invention is drawn to methods and compositions for use in decontaminating surfaces contaminated with chemical and/or biological warfare agents.

BACKGROUND OF THE INVENTION

Biological and chemical warfare agents are potent killing tools. Although they were banned by the Biological Weapons Convention of 1972 and the Chemical Weapons Convention of 1993, both chemical and biological weapons remain a legitimate and viable threat against people and countries throughout the world. As such, the need exists for an fast and effective means for decontaminating surfaces contaminated with biological and/or chemical agents.

SUMMARY OF THE INVENTION

It has been recognized that it would be desirable to provide a method and an associated decontaminating composition which would be effective against biological and/or chemical warfare agents. In accordance with this, a method for decontaminating a surface contaminated with a chemical or biological warfare agent can comprise contacting said surface with an effective amount of a composition. The composition includes an aqueous vehicle with water and from 0.001 wt % to 40.0 wt % of a peroxygen. The composition further includes from 0.001 ppm to 50,000 ppm by weight of a transition metal or alloy thereof based on the aqueous vehicle content.

Additional features and advantages of the invention will be apparent from the detailed description that follows, which illustrates, by way of example, features of the invention.

DETAILED DESCRIPTION OF THE PREFERRED EMBODIMENT(S)

Reference will now be made to the exemplary embodiments, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention. It is also to be understood that the terminology used herein is used for the purpose of describing particular embodiments only. The terms are not intended to be limiting unless specified as such.

It must be noted that, as used in this specification and the appended claims, the singular forms "a," "an," and "the" include plural referents unless the content clearly dictates otherwise.

The term "decontaminate" does not require that complete decontamination occur. In other words, partial decontamination to complete decontamination are included whenever the term "decontaminate," "decontaminating," "decontamination," etc. is used. Further, the use of the term "disinfect," "disinfecting," "disinfection," or the like, is used to include not only fighting infection of virus, bacteria, or other living organisms that may be used for biological warfare, but also includes decontamination of surfaces that are exposed to harmful chemicals often used in chemical warfare, such as by oxidation of the chemical. Again, complete disinfection is not required for disinfection to occur. Generally, though sanitizers, sterilants and disinfectants are used for the same purpose, i.e. to kill bacteria and/or viruses, etc., a sterilant composition exhibits a greater kill level compared to a disinfectant, which in turn has a better kill level than a sanitizer. This being stated, most applications require only sanitizer or disinfectant levels bacteria/virus reduction, though other applications benefit considerably from the use of sterilants. For convenience, in the present application the term "disinfectant" is used generally to refer to each of sanitizers, disinfectants, and sterilants unless the context clearly dictates otherwise.

The term "solution" is also used throughout the specification to describe the liquid compositions of the present invention. However, as these "solutions" include colloidal transition metals, these compositions can also be described as dispersions or suspensions. As the continuous phase is typically a solution, and the transition metal is present as a colloid, for convenience, these compositions will typically be referred to as "solutions" herein The term "substantially free" when used with regard to the compositions of the present invention refers to the total absence of or near total absence of a specific compound or composition. For example, when a composition is said to be substantially free of aldehydes, there are either no aldehydes in the composition or only trace amounts of aldehydes in the composition.

The term "peroxygen" refers to any compound containing a dioxygen (O—O) bond. Dioxygen bonds, particularly bivalent O—O bonds, are readily cleavable thereby allowing compounds containing them to act as powerful oxidizers. Non-limiting examples of classes of peroxygen compounds include peracids, peracid salts, and peroxides, such as hydrogen peroxide.

The term "biological warfare agent" and "biological weapon" are interchangeable and refer to any biological organism or toxin that are often used as a weapon of war or terrorism to kill, injure, or incapacitate. Similarly, the terms "chemical warfare agent" or "chemical weapon" refers to chemical agents which have toxic properties and can be used in war or terrorism to kill, injure, or incapacitate.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight ratio range of about 1 wt % to about 20 wt % should be interpreted to include not only the explicitly recited limits of 1 wt % and about 20 wt %, but also to include individual weights such as 2 wt %, 11 wt %, 14 wt %, and sub-ranges such as 10 wt % to 20 wt %, 5 wt % to 15 wt %, etc.

In accordance with this, the present invention provides a method for decontaminating surfaces contaminated with biological and/or chemical weapons. The method involves contacting the contaminated surface with a composition comprising an aqueous vehicle, including water and from 0.01 wt % to 30.0 wt % of a peroxygen. Additionally, from 0.001 ppm to 50,000 ppm by weight of a transition metal based on the aqueous vehicle content can also be present.

It is noted that the lower end of the range of the peroxygen can be modified to 0.01 wt %, 0.05 wt %, and 0.1 wt % and/or the upper end of the range can be modified to 30 wt %, 20 wt %, or 10 wt % in accordance with specific embodiments of the present invention. Further, the concentration of the metal content, including ionic and/or colloidal metal content, can also be modified to 10 ppm by weight at the lower end of the range, and/or to 20,000 ppm or 10,000 ppm by weight at the upper end of the range. As these ranges are merely exemplary, one skilled in the art could modify these ranges for a particular application, considering such things as the type of alcohol (polyhydric, food grade, mixtures, etc.); the type of peroxygen (peroxide, peracid, combination of peroxide/peracid, etc.); and the type of metal (ionic, colloidal, alloy, etc.). For example, in treating a human for exposure to biological or chemical agents, lower amounts of peracid may be used so as to be within safe parameters, whereas when decontaminating terra firma, facilities, or equipment, higher concentrations of the peracid may be useable (closer to the 40 wt %). Alternatively, if hydrogen peroxide is used as the peroxygen compound, then a broader range of the material may be useable for a wider range of applications.

The aqueous vehicle can optionally include other ingredients, such as organic co-solvents. In particular, certain alcohols can be present. It is noted that if an alcohol is present, it can be present at from 0.05 wt % to 40 wt %, with the lower end of the range of the alcohol being modifiable to 0.05 wt % or 0.1 wt %, and the upper end of the range being modifiable to 20 wt % or 10 wt %. In selecting the type of alcohol that can be used, for example, alcohols, including aliphatic alcohols and other carbon-containing alcohols, having from 1 to 24 carbons ($C_1$-$C_{24}$ alcohol) can be used. It is to be noted that "$C_1$-$C_{24}$ alcohol" does not necessarily imply only straight chain saturated aliphatic alcohols, as other carbon-containing alcohols can also be used within this definition, including branched aliphatic alcohols, alicyclic alcohols, aromatic alcohols, unsaturated alcohols, as well as substituted aliphatic, alicyclic, aromatic, and unsaturated alcohols, etc. In one embodiment, the aliphatic alcohols can be $C_1$ to $C_5$ alcohols including methanol, ethanol, propanol and isopropanol, butanols, and pentanols, due to their availability and lower boiling points. This being stated, polyhydric alcohols can also be used effectively in enhancing the disinfectant and sterilant potency of the compositions of the present invention, as well as provide some degree of added stabilization. Examples of polyhydric alcohols which can be used in the present invention include but are not limited to ethylene glycol (ethane-1,2-diol) glycerin (or glycerol, propane-1,2,3-triol), and propane-1,2-diol. Other non-aliphatic alcohols may also be used including but not limited to phenols and substituted phenols, erucyl alcohol, ricinolyl alcohol, arachidyl alcohol, capryl alcohol, capric alcohol, behenyl alcohol, lauryl alcohol (1-dodecanol), myristyl alcohol (1-tetradecanol), cetyl (or palmityl) alcohol (1-hexadecanol), stearyl alcohol (1-octadecanol), isostearyl alcohol, oleyl alcohol (cis-9-octadecen-1-ol), palmitoleyl alcohol, linoleyl alcohol (9Z, 12Z-octadecadien-1-ol), elaidyl alcohol (9E-octadecen-1-ol), elaidolinoleyl alcohol (9E, 12E-octadecadien-1-ol), linolenyl alcohol (9Z, 12Z, 15Z-octadecatrien-1-ol), elaidolinolenyl alcohol (9E, 12E, 15-E-octadecatrien-1-ol), combinations thereof and the like.

In some embodiments, for practical considerations, methanol, ethanol, and denatured alcohols (mixtures of ethanol and smaller amounts of methanol, and optionally, minute amounts of benzene, ketones, acetates, etc.) can often be preferred for use because of their availability and cost. Glycerol is also preferable for use in some embodiments. If the desire is to provide a food grade composition, as may be desirable for mucosal, skin, or alimentary canal application, then alcohols can be selected that satisfy this requirement. As these ranges are merely exemplary, one skilled in the art could modify these ranges for a particular application, considering such things as whether alcohol selected for use is polyhydric, whether the alcohol is food grade, mixtures of alcohols, etc.

Regarding the transition metal, in accordance with the embodiments of the present invention, the metal can be in ionic form (e.g. a metal salt) and/or colloidal form. In one specific embodiment, the transition metal can be in a submicron form (i.e. dispersion of less than 1 µm metal colloidal particles). However, larger colloidal transition metal particles can also be used in certain applications. Typical transition metals that are desirable for use include Group VI to Group XI transition metals, and more preferably, can include Group X to Group XI transition metals. Alloys including at least one metal from the Group VI to Group XI metals can also be used. It is recognized that any of these metals will typically be oxidized to the corresponding cation in the presence of a peroxygen. However, with colloidal metals, typically, the surface is usually more susceptible to such oxidation. Further, when colloidal metals are dispersed in a colloidal solution, there is often an amount of the metal in ionic or salt form that is also present in the suspension solution. For example, colloidal silver may include a certain percentage of a silver salt or ionic silver in solution, e.g., 10% to 90% by weight of metal content can be ionic based on the total metal content. This being stated, certain preferred metals for use in accordance with embodiments of the present invention are ruthenium, rhodium, osmium, iridium, palladium, platinum, copper, gold, silver, alloys thereof, and mixtures thereof. Silver is often the most preferred, depending on the application, the levels of kill that are desired or required, the type of pathogen being targeted, the substrate that is being cleaned, etc. Any of these embodiments can also benefit from the use of alloys. For Example, certain combinations of metals in an alloy may provide an acceptable kill level for a specific pathogen, and also provide benefits that are related more to secondary consideration, such as solution stability, substrate to be cleaned, etc. Preferred examples of transition metal alloys for use in the present invention include but are not limited to copper-silver allows, silver-manganese alloys, Iron-copper alloys, chromium-silver alloys, gold-silver alloys, and magnesium-silver alloys.

Exemplary colloidal silvers that can be used include those sold by Solutions IE, Inc. under the trade names CS Plus and C S Ultra. Other colloidal silver products that can be used as the silver source include ASAP, Sovereign Silver, Silver Max, and the like. If used in ionic form, preferred silver salts include but are not limited to silver nitrate, silver acetate, silver citrate, silver oxide, and silver carbonate. In one embodiment, the colloidal particles used in the present invention can have a particle size range of from 0.001 µm to 1.0 µm. In another embodiment the colloidal transition metal particles can have a size range of from 0.030 µm to 0.5 µm. In still another embodiment the average particle size is 0.35 µm to 0.45 µm. Though any colloidal silver solution that is functional for use in the formulations of the present invention can be used, in one embodiment, it can be desirable to use RO water as the suspension medium for the colloidal silver that is mixed with the other ingredients. In a more detailed aspect, the RO water can also be distilled, resulting in 18-20 MΩ water, though this is not required.

The peroxygen component of the disinfectant solution can be a single compound or a combination of multiple peroxygen compounds or peroxygen forming compounds. The peroxygen portion of the disinfectant formulation can range from about 0.001 wt % to about 40.0 wt %. In one embodiment the range can be from 0.05 wt % to 30.0 wt %. In another embodiment the range can be from 0.1 to 20 wt %. In yet another embodiment the range can be from 0.5 wt % to 10 wt %.

In one embodiment, the peroxygen can be any aliphatic or aromatic peracid (or peroxyacid) that is functional for disinfectant purposes in accordance with embodiments of the present invention. While any peroxyacid could be used, peroxyacids containing from 1 to 7 carbons are the most practical for use. These peroxyacids can include, but not be limited to, peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, and/or peroxybenzoic acid and mixtures thereof. The peroxyacid used in the present invention can be prepared using any method known in the art. When the peroxyacid is prepared from an acid and hydrogen peroxide, the resultant mixture contains both the peroxyacid and the corresponding acid that it is prepared from. For example, in embodiments that utilize peroxyacetic acid, the presence of the related acid (acetic acid) provides stability to the mixture, as the reaction is an equilibrium between the acid, hydrogen peroxide, and the peroxyacid and water, as follows:

$$H_2O_2 + CH_3COOH \longleftrightarrow CH_3COO-OH + H_2O$$

Peracid salts, such as salts of the above listed peracids, can also be included in peroxygen component of the disinfectant solutions. Non-limiting examples of such salts include permanganates, perborates, perchlorates, peracetates, percarbonates, persulphates, and the like. The salts can be used alone or in combination with each other or other peroxygen compounds to form the peroxygen component of the invention.

In another embodiment, the peroxygen component of the invention can include a peroxide compound. While hydrogen peroxide is considered to be desirable peroxide for use in accordance with embodiments of the present invention, other peroxides can also be used, such as metal peroxides and peroxyhydrates. The metal peroxides that can be used include, but are not limited to, sodium peroxide, magnesium peroxide, calcium peroxide, barium peroxide, and/or strontium peroxide. Other salts (for example sodium percarbonate) have hydrogen peroxide associated therewith much like waters of hydration, and these could also be considered to be a source of hydrogen peroxide, thereby producing hydrogen peroxide in situ. Generally, when peroxides are used in the peroxygen component of the present invention they are used in combination with other non-peroxide peroxygen compounds, e.g. peracids.

The compositions of the present invention can be prepared for application by any of a number of methods. For example, the composition can be prepared as a solution, gel, foam, spray, etc. As a solution, the composition can be used as a liquid dispersion bath for dipping instruments or other objects, as a spray for applying to less mobile objects, as a wipe where the liquid dispersion is applied to a fabric or fabric-like material for easy application without the need for spray or other application methods, as a topical dressing, as a mouthwash, etc. In other words, any application method known by those skilled in the art can be utilized in accordance with embodiments of the present invention. In one embodiment, the composition can contact the contaminated surface by spraying. In another embodiment, the composition can contact the contaminated surface by wiping. In another embodiment, the composition can contact the contaminated surface by submersion in the composition. In yet another embodiment, the composition can contact the contaminated surface by pouring or splashing.

As described, this composition can be used against both chemical and biological warfare agents with relative to complete safety to humans and other mammals. Examples of biological agents which the composition can be used for include but are not limited to those which cause anthrax, ebola, bubonic plague, cholera, tularemia, brucellosis, Q fever, machupo, coccidioides mycosis, glanders, melioidosis, shigella, rocky mountain spotted fever, typhus, psittacosis, yellow fever, Japanese B encephalitis, rift valley fever, and/or smallpox. Examples of chemical warfare agents which the composition can be used for include but are not limited to tabun, sarin, soman, cyclohexyl methylphosphonofluoridate, VX, mustard agent (gas), hydrogen cyanide, arsines, phencyclidine, ricin, abrin, and/or agent 15.

The types of surfaces which can be sterilized or decontaminated under the present invention are wide ranging. Non-limiting examples of types of surfaces include skin, hair, mucosal tissue, alimentary canal tissue, metals, fabrics, plastics, glass, composites, woods, and terra firma. The surfaces can be smooth or porous, although some application or contacting methods may be more effective with certain surface types.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Preparation of Disinfectant

An aqueous disinfectant composition is prepared in accordance with embodiments of the present invention, which includes the following ingredients in approximate amounts: 9 wt % ethanol; 1.3 wt % peroxyacetic acid (from a 6 wt % solution); less than 3 wt % hydrogen peroxide to stabilize the peroxyacetic acid; and the balance being water containing 600 ppm colloidal silver. It is noted that there will be less than 600 ppm by weight of the colloidal silver when based on the aqueous vehicle content as a whole.

Example 2

Preparation of Disinfectant

An aqueous disinfectant composition is prepared in accordance with embodiments of the present invention, which includes the following ingredients in approximate amounts: 9 wt % isopropanol; 1.3 wt % peroxypropanoic acid (from a 6 wt % solution); less than 3 wt % of a peroxide, e.g., sodium peroxide, to stabilize the peroxypropanoic acid; and the balance being water containing 600 ppm ionic silver. It is noted that there will be less than 600 ppm by weight of the ionic silver when based on the aqueous vehicle content as a whole.

Example 3

Preparation of Disinfectant

An aqueous disinfectant composition is prepared in accordance with embodiments of the present invention, which includes the following ingredients in approximate amounts: 20 wt % denatured alcohol; 5 wt % peroxyformic acid; and the balance being water containing 10,000 ppm by weight colloidal silver and copper alloy. Small amounts of hydrogen peroxide and formic acid are also added to the composition as a whole to stabilize the peroxyformic acid. It is noted that there will be less than 10,000 ppm by weight of the colloidal silver when based on the aqueous vehicle content as a whole.

Example 4

Preparation of Disinfectant

An aqueous disinfectant composition is prepared in accordance with embodiments of the present invention, which includes the following ingredients in approximate amounts: 9 wt % ethanol; 1.3 wt % peroxyacetic acid (from a 6 wt % solution); less than 3 wt % hydrogen peroxide to stabilize the peroxyacetic acid; and the balance being water containing 80 ppm colloidal silver. It is noted that there will be less than 80 ppm by weight of the colloidal silver when based on the aqueous vehicle content as a whole.

Example 5

Preparation of Disinfectant

An aqueous disinfectant composition is prepared in accordance with embodiments of the present invention, which includes the following ingredients in approximate amounts: 10 wt % glycerol; 1.3 wt % peracetic acid; and the balanced being water with approximately 300 ppm colloidal silver. It is noted that there will be less than 300 ppm by weight of the colloidal silver when based on the aqueous vehicle content as a whole.

Example 6

Preparation of Disinfectant

An aqueous disinfectant composition is prepared in accordance with embodiments of the present invention, which includes the following ingredients in approximate amounts: 10.0 wt % glycerol; 1.8 wt % percitric acid; and the balance being water with approximately 300 ppm colloidal silver. It is noted that there will be less than 300 ppm by weight of the colloidal silver when based on the aqueous vehicle content as a whole.

Example 7

Preparation of Disinfectant

An aqueous disinfectant composition is prepared in accordance with embodiments of the present invention, which includes the following ingredients in approximate amounts: 8.5 wt % 1-propanol; 1.3 wt % peracetic acid; and the balance being RO water (reverse osmosis water) containing about 300 ppm by weight colloidal silver. It is noted that there will be less than 300 ppm by weight of the colloidal silver when based on the aqueous vehicle content as a whole.

Example 8

Preparation of Disinfectant

An aqueous disinfectant composition is prepared in accordance with embodiments of the present invention, which includes the following ingredients in approximate amounts: 40 wt % glycerol; 8 wt % percitric acid; and the balance being RO water (reverse osmosis water) containing about 300 ppm by weight colloidal silver. It is noted that there will be less than 300 ppm by weight of the colloidal silver when based on the aqueous vehicle content as a whole.

Example 9

Preparation of Disinfectant

An aqueous disinfectant composition is prepared in accordance with embodiments of the present invention, which includes the following ingredients in approximate amounts: 8.5 wt % glycerol; 0.4 wt % peracetic acid; and the balance being RO water (reverse osmosis water) containing 300 ppm by weight colloidal silver. It is noted that there will be less than 300 ppm by weight of the colloidal silver when based on the aqueous vehicle content as a whole.

Example 10

Kill-time Studies of *Staphylococcus aureus* Using Disinfectant of Example 1

A study was conducted to determine the antimicrobial activity of the colloidal silver-containing disinfectant of Example 1, when challenged with an organic load, on the test organism *Staphylococcus aureus*. This was accomplished by performing a standard suspension test on the disinfectant containing 5% v/v horse serum. A 15 second contact time was evaluated.

Specifically, the test suspension was prepared by growing a 5 ml culture of *Staphylococcus aureus*, ATCC 6538, in Todd Hewitt Broth at 37° C., for 20 hours. Five (5) ml of culture was pelleted by centrifugation, washed with 5 ml sterile 18 MΩ water, centrifuged again, and resuspended in a final volume of 5 ml sterile water.

A neutralizer was prepared that consisted of 9 ml tubes of 12.7 wt % Tween 80 (surfactant), 6.0 wt % Tamol, 1.7 wt % lecithin, 1 wt % peptone, and 0.1 wt % cystine, to which was added 10 pd of catalase solution (Sigma, C100, 42,300 units/mg).

The "Kill Time" procedure followed was as follows: A 9.9 ml aliquot of the disinfectant of Example 1 (containing 5% v/v horse serum) was placed in a sterile 20 mm×150 mm tube, and the tube was equilibrated in a 20° C. water bath. The tube of disinfectant was inoculated with 100 µl of the test organism suspension at time zero. After 15 seconds, 1 ml of the organism/disinfectant suspension was removed to 9 ml of neutralizer. After 2 minutes, the neutralized suspension was serially diluted (1:1×10, 1:1×10$^2$, 1:1×10$^3$, etc.) in physiological saline solution (PSS). The number of viable organisms in selected dilution tubes was assayed by membrane filtration. One (1) ml aliquots were plated in duplicate, and the membranes were washed with about 100 ml of sterile PSS and removed to Columbia agar plates. The plates were incubated at 37° C. for 20 hours. The number of colonies on each filter was counted and log reduction and percent kill values were computed.

As a control, a titer (or measurement of the amount or concentration of a substance in a solution) of the test suspension was computed by performing membrane filtration assays of selected 1:10 dilutions of the test suspension in PSS. A neutralizer control was performed by inoculating a mixture of 9 ml of neutralizer and 1 ml of disinfectant with 100 µl of the 1:10$^5$ dilution of the titer. This produced about 1,500 CFU/ml in the tube, which was allowed to stand for 20 minutes prior to dilution and assay of the tubes by membrane filtration using duplicate 1 ml samples. Sterilization controls were performed by filtering 100 ml (PSS) or 1 ml (other fluids) samples of each solution used in this testing. Plates were incubated as above.

The results are provided as follows:

TABLE 1a

| | Titer | | |
|---|---|---|---|
| Dilution | 1:1 × 10$^5$ | 1:1 × 10$^6$ | 1:1 × 10$^7$ |
| Number of Colonies | TNC* TNC | TNC TNC | 111 89 |

*TNC—Too Numerous to Count

TABLE 1b

| Disinfectant solution (Example 1 solution with 5% v/v horse serum) Dilution of *staphylococcus*/disinfectant suspension | | | |
|---|---|---|---|
| Dilution | 1:1 × 10$^1$ | 1:1 × 10$^2$ | 1:1 × 10$^3$ |
| 15 Seconds | 0 0 | 0 0 | 0 0 |

TABLE 1c

| | Neutralization control | |
|---|---|---|
| Dilution | undilute | 1:1 × 10$^1$ |
| 15 Seconds | TNC TNC | 156 148 |

Sterilization controls indicated zero growth for the neutralizer, water, PSS, Columbia agar, disinfectant, and horse serum. Results of the titer showed a viable staphylococcus concentration of 1×10$^{10}$ organisms per ml in the original suspension. Inoculation of 9.9 ml of disinfectant with 100 µl of this suspension produced an initial concentration of 1×10$^8$ organisms per ml in the assay tube. Results from these procedures allowed log reduction (LR) and percent kill (PK) values to be calculated using the formulas: 1) LR=−Log(S/So) where S=concentration of viable organisms after 45 minutes; and So=the initial concentration of viable organisms at time zero; and 2) PK=(1−(S/So))×100. These values are shown below.

TABLE 2

| | Results | | |
|---|---|---|---|
| Solution | Contact Time | Log Reduction (LR) | Percent Kill (PK) |
| Disinfectant solution of Example 1 with 5% v/v horse serum | 15 sec | >7.00 | >99.99999 |

The neutralization control data indicated that the test solution was adequately neutralized. Observed counts were slightly greater than those expected, indicating no residual killing took place due to un-neutralized disinfectant. In general, the disinfectant solution tested here had high antimicrobial activity against *Staphylococcus aureus*. It is significant to note that this level of activity was achieved even though the disinfectant was premixed with an organic load consisting of 5% v/v horse serum. An organic load (such as 5% v/v horse serum) will often adversely affect the antimicrobial action of disinfectants. The solution of Example 1 was nevertheless able to effect greater than a 7 log reduction of viable organisms within 15 seconds, even in the presence of 5% v/v horse serum.

Example 11

Kill-time Studies of *Bacillus subtilis* Using Disinfectant of Example 6

A study was conducted to determine the antimicrobial activity of the colloidal silver-containing disinfectant of Example 6, on bacterial endospores from the test organism *Bacillus subtilis*. This was accomplished by performing a standard kill-time suspension test using a suspension of *B. subtilis* endospores.

Specifically, the test suspension containing endospores from *B. subtilis* was prepared from a culture grown for three days at 37° C. in Leighton-Doi medium. The suspension was placed at 65° C. for 30 minutes to kill vegetative organisms, and then centrifuged to pellet the spores. Spores were resuspended in sterile HPLC water and allowed to set overnight at 4° C. This washing/setting process was repeated a total of three times. The final spore suspension was examined for purity using phase-contrast microscopy and stored at 4° C. until it was used.

A neutralizer was prepared that consisted of 9 ml tubes of 12.7 wt % Tween 80 (surfactant), 6.0 wt % Tamol, 1.7 wt % lecithin, 1 wt % peptone, and 1.0 wt % cystine and 500 mM Tris (pH 7.85), to which 100 µl of catalase solution (Sigma C100, 42,300/mg) was added immediately before use.

The "Kill Time" procedure followed was as follows: A 9.9 ml aliquot of the disinfectant of Example 6 (containing 5% v/v horse serum) was placed in a sterile 50 ml polypropylene centrifuge tube, and the tube was equilibrated in a 20° C. water bath. The tube of disinfectant was inoculated with 100 µl of the spore/disinfectant suspension at time zero. After 60 seconds, 1 ml of the spore/disinfectant suspension was removed to 9.1 ml of neutralizer. After 2 minutes, the neutralized suspension was serially diluted (1:1×10, 1:1×10$^2$, 1:1×10$^3$, etc.) in physiological saline solution (PSS). The number of viable spores in selected dilution tubes was assayed by membrane filtration. One (1) ml aliquots were plated in duplicate, and the membranes were washed with about 100 ml of sterile PSS and removed to Columbia agar plates. The plates were incubated at 37° C. for 20 hours. The number of colonies on each filter was counted and log reduction and percent kill values were computed.

As a control, a titer (or measurement of the amount or concentration of a substance in a solution) of the test suspension was computed by performing membrane filtration assays of selected 1:10 dilutions of the test suspension in PSS. A neutralizer control was performed by inoculating a mixture of 9.1 ml of neutralizer and 1 ml of disinfectant with 100 µl of the 1:10$^6$ dilution of the titer. This produced about 96 CFU/ml in the tube, which was allowed to stand for 20 minutes prior to dilution and assay of the tubes by membrane filtration using duplicate 1 ml samples. Sterilization controls were performed by filtering 100 ml (PSS) or 1 ml (other fluids) samples of each solution used in this testing. Plates were incubated as above.

The results are provided as follows:

TABLE 15a

| | Titer | | |
|---|---|---|---|
| Dilution | 1:1 × 10$^7$ | 1:1 × 10$^8$ | 1:1 × 10$^9$ |
| Number of | TNC* | 78 | 12 |
| Colonies | TNC | 74 | 5 |

*TNC—Too Numerous to Count

TABLE 15b

| Disinfectant solution (Example 6 solution) Dilution of B. subtilis spores/disinfectant suspension | | | | |
|---|---|---|---|---|
| Dilution | 1:1 × 10$^2$ | 1:1 × 10$^3$ | 1:1 × 10$^4$ | 1:1 × 10$^5$ |
| 3 minutes | TNC | TNC | 209 | 30 |
| | TNC | TNC | 331 | 34 |

TABLE 15c

| Disinfectant solution (Example 6) Dilution of B. subtilis spores/disinfectant suspension | | | | |
|---|---|---|---|---|
| Dilution | 1:1 × 10$^2$ | 1:1 × 10$^3$ | 1:1 × 10$^4$ | 1:1 × 10$^5$ |
| 10 minutes | 0 | 0 | 0 | 0 |
| | 0 | 0 | 0 | 0 |

TABLE 15d

| Neutralization control |
|---|
| Undiluted |
| 76 |
| 83 |

TABLE 15e

| Sterility controls | |
|---|---|
| Material | Counts |
| Example 6 Disinfectant | 0 |
| Neutralizer | 0 |
| Columbia Agar | 0 |
| Physiological sterile saline | 0 |

Results of the titer showed a viable *B. subtilis* spore concentration of 9.80×10$^9$ spores per ml in the original suspension. Inoculation of 9.9 ml of disinfectant with 100 µl of this suspension produced an initial concentration of 9.80×10$^7$ spores per ml in the assay tube. Results from these procedures allowed log reduction (LR) and percent kill (PK) values to be calculated using the formulas: 1) $LR=-\mathrm{Log}(S/So)$ where $S$=concentration of viable organisms after 45 minutes; and $So$=the initial concentration of viable organisms at time zero; and 2) $PK=(1-(S/So))\times 100$. These values are shown below.

TABLE 16

| Results | | | |
|---|---|---|---|
| Solution | Contact Time | Log Reduction (LR) | Percent Kill (PK) |
| Disinfectant solution of Example 6 | 3 minutes | 1.38 | 95.79 |
| Disinfectant solution of Example 6 | 10 minutes | >7.18 | 99.999993 |

The neutralization control data indicated that the test solution was adequately neutralized. Observed counts were similar to, or higher than those expected, indicating no residual killing took place due to un-neutralized disinfectant. The disinfectant solution of Example 6 had good sporicidal activity, effecting a 1.38 log reduction within 3 minutes and greater than 7 log reduction in 10 minutes. It is worth noting that *B. subtilis* is a common species used in sporacidal testing and belongs to the same genus as the organism that causes anthrax. Because of their similarities, *B. subtilis* spores have been used as non-pathogenic surrogates for spores of *Bacillus anthracis*.

Example 12

Kill-time Studies of *Mycobacterium bovis* Using the Disinfectant Solution of Example 5

A study was conducted to determine tuberculocidal activity of the disinfectant solution of Example 5 on a hard surface using the CRA Environmental Wipe Method. This method is fully described in: Christensen, R. P., R. A. Robison, D. F. Robinson, B. J. Ploeger, R. W. Leavitt, and H. L. bodily, Antimicrobial Activity of Environmental Surface Disinfecants in the Absence and Presence of Bioburden. Journal of the American Dental Association, 119:493-505. 1989.

Specifically, a test suspension containing *Mycobacterium bovis* (ATCC # 35743) was prepared from a frozen suspension of a standardized culture grown in modified Proskauer-Beck medium. The suspension was thawed and mixed with an equal volume of phosphate-buffered gelatin solution in a Teflon-on-glass tissue grinder on ice. The suspension was homogenized for two minutes, then diluted 1:4 in physiological saline solution (PSS) containing 0.1% Tween 80. The suspension was vortexed and held on ice until used in inoculate the test surface.

A neutralizer mixture consisted of 50 ml flasks of Tryptic soy broth containing 1.0% Tween 80, 1.0% lecithin, and 50 µl of concentrated catalase solution (Sigma, C100, 42,300 units/mg).

The CRA environmental Wipe Method which was used is detailed below. An 8×12 inch piece of laminated plastic counter covering was secured to polypropylene dental trays (size B, Zirc Dental) with silicone adhesive. Lids and trays were sterilized by a hydrogen peroxide gas plasma sterilizer. Two ml of test organism suspension was applied to the surface with a sterile 2×2-in cotton-filled gauze sponge. The surface was allowed to dry 20-30 minutes in a biosafety cabinet under laminar flow. Then 3.5 ml of disinfectant (or water) was applied to a sterile gauze sponge, which was used to wipe the inoculated test surface for 10 seconds using about 150-g pressure with overlapping strokes (20 left to right, followed by 20 top to bottom). After 3 minutes, the trays were flooded with 50 ml of neutralizer and scrubbed for 1 minute with a sterile polypropylene brush to remove and suspend organisms. The fluid was collected and serially diluted 1:10 in physiological saline solution (PSS). The number of viable organisms in selected dilution tubes was assayed by membrane filtration. One ml aliquots were plated in duplicate. The membranes were washed with about 100 ml of sterile PSS and removed to *Mycobacteria* 7H11 agar plates. The plates were incubated at 37° C. for about three weeks. The number of colonies on each was counted and log reduction and percent kill values were computed.

As a control, a titer of the test suspension was computed by performing membrane filtration assays of selected 1:10 dilutions of the test suspension in PSS. A neutralizer control was performed by inoculating a mixture of 9 ml of neutralizer and 1 ml of disinfectant with 100 µl of the 1:$10^3$ dilution of the titer containing 1750 CFU. This produced 175 CFU/ml in the tube, which was allowed to stand for 20 minutes prior to dilution and assay of the tubes by membrane filtration using duplicate 1 ml samples.

The results are provided as follows:

TABLE 19a

| *Mycobacterium bovis* Titer | | | |
|---|---|---|---|
| Dilution | 1:1 × $10^3$ | 1:1 × $10^4$ | 1:1 × $10^5$ |
| Number of Colonies | TNC* | TNC | 175 |
| | TNC | TNC | 174 |

*TNC—Too Numerous to Count

TABLE 19b

| Disinfectant solution of Example 5 Dilution of *M. bovis*/disinfectant suspension | | | | |
|---|---|---|---|---|
| Dilution | Undiluted | 1:1 × $10^1$ | 1:1 × $10^2$ | 1:1 × $10^3$ |
| 3 minutes | 1 | 0 | 0 | 0 |
| | | 0 | 0 | 0 |

TABLE 19c

| Neutralization control |
|---|
| Undiluted |
| 75 |
| 66 |

TABLE 19d

| Sterility controls | |
|---|---|
| Material | Counts |
| Phosphate buffered gelatin | 0 |
| Neutralizer + catalas | 0 |
| Example 5 Disinfectant | 0 |
| Mycobacteria 7H11 Agar | 0 |
| Physiological sterile saline (PSS) + 0.1% Tween 80 | 0 |
| Physiological sterile saline (PSS) | 0 |

Results of the titer showed the initial concentration of *M. bovis* was 1.75×107 CFU per ml in the prepared suspension. Inoculation of the test surface following drying produced a challenge exhibited by the water control. The initial concentration of viable bacilli on the test surface (So) was 2.63×$10^5$. Results from these procedures allowed log reduction (LR) and percent kill (PK) values to be calculated using the formulas: 1) LR=–Log(S/So) where S=concentration of viable organisms after a period of exposure to the disinfectant; and So=the initial concentration of viable organisms at time zero; These values are shown in the Table 20 below.

TABLE 20

| Results | | | |
|---|---|---|---|
| Solution | Contact Time | Log Reduction (LR) | Percent Kill (PK) |
| Example 5 | 3 minutes | 5.02 | 99.99905 |

The neutralization control data indicated that each test solution was adequately neutralized. Observed counts were similar to those expected from the titer data.

Example 13

Kill-time Studies of Sporicidal Activity Using Various Disinfectant Solutions A study was conducted to determine the antimicrobial activity of the silver-containing disinfectant of Example 5 on bacterial endospores from the test organism *Bacillus subtilis*. This was accomplished by performing a standard kill-time suspension test using a suspension of *B. subtilis* endospores. In general, spores are much more difficult to kill than common bacteria.

The test suspension containing endospores from *Bacillus subtilis* (ATCC # 19659) was prepared from a culture grown for three days at 37° C. in Leighton-Doi medium. The suspension was placed at 65° C. for 30 minutes to kill vegetative organisms, then centrifuged to pellet the spores. Spores were resuspended in sterile HPLC water and allowed to set overnight at 4° C. This washing/setting process was repeated a total of three times. The final spore suspension was examined for purity using phase-contrast microscopy and stored at 4° C. until used.

A neutralizer solution was also prepared that consisted of 9 ml tubes of 12.7 wt % Tween 80, 6.0 wt % Tamol, 1.7 wt % lecithin, 1 wt % peptone, and 1.0 wt % cystine, and 500 mM tris (pH 7.85), to which 100 μl of catalase solution (Sigma, C100, 42,300 units/mg) was added immediately before use.

The "kill time" procedure was as follows: A 9.9 ml aliquot of the disinfectant was placed in a 50 ml polypropylene sterile centrifuge tube. The tube was equilibrated in a 20° C. water bath. The tube of disinfectant was inoculated with 100 μl of the spore suspension at time zero. After a 30 second contact time, one ml of spore/disinfectant suspension was removed to 9.1 ml of neutralizer. The tubes were mixed thoroughly. After 2 minutes, the neutralized suspension was serially diluted 1:10, in physiological saline solution in physiological saline solution (PSS). The number of viable spores in selected dilution tubes was assayed by membrane filtration. One (1) ml aliquots were plated in duplicate. The membranes were washed with about 100 ml of sterile PSS and removed to Columbia agar plates. The plates were incubated at 37° C. for 20 hours. The number of colonies on each filter was counted and log reduction and percent kill values were computed.

As a control, a titer of the test suspension was computed by performing membrane filtration assays on selected 1:10 dilutions in PSS of the test suspension. A neutralizer control was performed by inoculating a mixture of 9.1 ml of neutralizer and 1 ml of disinfectant with 100 μl of the $1:1\times10^6$ dilution of the titer. This produced about 130 CFU/ml in the tube, which was allowed to stand for 20 minutes prior to dilution and assay by membrane filtration using duplicate 1 ml samples.

The results are provided as follows:

TABLE 23a

| | Bacillus Subtilis Titer | | |
|---|---|---|---|
| Dilution | $1:1\times10^7$ | $1:1\times10^8$ | $1:1\times10^9$ |
| Number of Colonies | TNC* TNC | 106 115 | 10 15 |

*TNC—Too Numerous to Count

TABLE 23b

| Disinfectant solution (Example 5) Dilution of B. subtilis spores/disinfectant suspension | | | |
|---|---|---|---|
| Dilution | $1:1\times10^2$ | $1:1\times10^3$ | $1:1\times10^4$ |
| 30 Seconds | 0 0 | 0 0 | 0 0 |

TABLE 23c

| Neutralization control |
|---|
| Undiluted |
| 135 |
| 118 |

TABLE 23d

| Sterility Controls | |
|---|---|
| Material | Counts |
| PSS | 0 |
| Neutralizer | 0 |
| Columbia Agar | 0 |
| Example 5 | 0 |
| Example 7 | 0 |

Results of the titer showed a viable B. subtilis spore concentration of $1.11\times10^{10}$ spores per ml in the original suspension. Inoculation of 9.9 ml of disinfectant with 100 μl of this suspension produced an initial concentration of $1.11\times10^8$ spores per ml in the assay tube. Results from these procedures allowed log reduction (LR) and percent kill (PK) values to be calculated using the formulas: 1) LR=−Log(S/So) where S=concentration of viable organisms after specified contact time, and So=the initial concentration of viable organisms at time zero; and 2) PK=(1−(S/So))×100. These values are shown below in Table 24.

TABLE 24

| | | Results | |
|---|---|---|---|
| Solution | Contact Time | Log Reduction (LR) | Percent Kill (PK) |
| Example 5 | 30 seconds | >7.05 | >99.999991 |
| Example 7 | 30 seconds | >7.05 | >99.999991 |

Neutralization control data revealed that the neutralizer was able to adequately neutralize this disinfectant. Observed counts were consistently higher than those expected. Each of the test disinfectant solutions (Examples 5 and 7) had rapid and potent sporicidal activity. Specifically, each of Examples 5 and 7 was able to achieve greater than 7-log reduction within 30 seconds. As a control, the same culture was tested using the same concentration of peracetic acid with none of the other active ingredients (i.e. without the alcohol or silver content). The compositions of Examples 5 and 7 exhibited a greater kill level by several orders of magnitude.

Example 14

Kill-time Studies of Sporicidal Activity Using 2.4% Alkaline Glutaraldehyde Disinfectant For comparison purposes, a study was conducted to determine the antimicrobial activity of a 2.4% alkaline glutaraldehyde disinfectant on bacterial endospores from the test organism Bacillus subtilis. Glutaraldehyde disinfectant solution is a common disinfectant used in hospitals to kill bacteria and other pathogens that might otherwise be difficult to kill. This study was carried out by performing a standard kill-time suspension test using a suspension of B. subtilis endospores. A 15 minute contact time was evaluated.

A test suspension containing endospores from Bacillus subtilis (ATCC # 19659) was prepared from a culture grown on Nutrient agar, to which additional sporulation enhancements were added. Plates were harvested with sterile water and endospores were purified by repeated centrifugations and resuspensions in water. The final wash was in 70 wt % ethanol for 30 minutes, to ensure the death of all vegetative bacteria. The spores were resuspended in water containing 0.1 wt % Tween 80 to prevent clumping and stored at 4° C. until used.

A neutralizer was prepared that consisted of 1 ml of freshly made, filter-sterilized sodium bisulfite solution at 5.28 wt %.

The "kill time" procedure was as follows: A 9.9 ml aliquot of the disinfectant was placed in a sterile glass culture tube. The tube was equilibrated in a 20° C. water bath. The tube of disinfectant, 9 ml of 2.4 wt % alkaline glutaraldehyde (Freshly activated CIDEXPLUS, 3.4%, Lot #:2002247TP—diluted to 2.4 wt % with sterile water), was inoculated with 100 µl of the test organism suspension at time zero. After 15 min, 1 ml of spore/disinfectant suspension was removed to 9 ml of neutralizer. The tube was mixed thoroughly. After 2 minutes, the neutralized suspension was serially diluted (1:1× 10, 1:1×10$^2$, 1:1×10$^3$, etc.) in physiological saline solution (PSS). The number of viable spores in selected dilution tubes was assayed by membrane filtration. One (1) ml aliquots were plated in duplicate. The membranes were washed with about 100 ml of sterile PSS and removed to Columbia agar plates. The plates were incubated at 37° C. for 20 hours. The number of colonies on each filter was counted and log reduction and percent kill values were computed.

As a control, a titer of the test suspension was computed by performing membrane filtration assays on selected 1:10 dilutions in PSS of the test suspension.

A neutralizer control was performed by inoculating a mixture of 1 ml of neutralizer and 1 ml of disinfectant with 100 µl of the 1:1×10$^5$ dilution of the titer. This produced about 450 CFU/ml in the tube, which was allowed to stand for 20 minutes prior to dilution and assay by membrane filtration using duplicate 1 ml samples.

The results are provided as follows:

TABLE 27a

| | Titer | | |
|---|---|---|---|
| Dilution | 1:1 × 10$^6$ | 1:1 × 10$^7$ | 1:1 × 10$^8$ |
| Number of Colonies | TNC* TNC | 96 93 | 0 0 |

*TNC—Too Numerous to Count

TABLE 27b

Disinfectant solution (2.4 wt % alkaline glutaraldehyde disinfectant) Dilution of *B. subtilis* spores/disinfectant suspension

| Dilution | 1:1 × 10$^1$ | 1:1 × 10$^2$ | 1:1 × 10$^3$ | 1:1 × 10$^4$ |
|---|---|---|---|---|
| 15 minutes | TNC TNC | TNC TNC | TNC TNC | 259 52 |

TABLE 27C

| | Neutralization control | |
|---|---|---|
| Dilution | 1:1 × 10$^1$ | 1:1 × 10$^2$ |
| 15 Seconds | 72 70 | 1 4 |

Sterilization controls indicated zero growth for the glutaraldehyde, sodium bisulfite, water, PSS, and Columbia agar. Results of the titer showed a viable *B. subtilis* spore concentration of 9.45×10$^8$ spores per ml in the original suspension. Inoculation of 9.9 ml of disinfectant with 100 µl of this suspension produced an initial concentration of 9.45×10$^6$ spores per ml in the assay tube. Results from these procedures allowed log reduction (LR) and percent kill (PK) values to be calculated using the formulas: 1) LR=−Log(S/So) where S=concentration of viable organisms after 1 hour, and So=the initial concentration of viable organisms at time zero; and 2) PK=(1−(S/So))×100. These values are shown below in Table 26.

TABLE 28

| | Results | | |
|---|---|---|---|
| Solution | Contact Time | Log Reduction (LR) | Percent Kill (PK) |
| Alkaline glutaraldehyde | 15 min | 0.48 | 67.1 |

Neutralization control data revealed that the neutralizer was able to adequately neutralize this disinfectant. Observed counts were greater than those expected. The 2.4 wt % alkaline glutaraldehyde solution tested had relatively slow sporicidal activity, producing only a 0.48 log-reduction in 15 minutes, which is significantly lower than that produced by any of the exemplary compositions above prepared in accordance with embodiments of the present invention.

Example 15

Kill-time Studies of *Mycobacterium bovis* Using Lysol® Spray

For comparison purposes, a study was conducted to determine tuberculocidal activity of a Lysol® spray disinfectant (Lysol Spray, spring waterfall scent Lot # B4194-NJ2 1413-A3) on a hard surface using the CRA Environmental Wipe Method. This method is fully described in: Christensen, R. P., R. A. Robison, D. F. Robinson, B. J. Ploeger, R. W. Leavitt, and H. L. bodily, Antimicrobial Activity of Environmental Surface Disinfecants in the Absence and Presence of Bioburden. Journal of the American Dental Association, 119:493-505. 1989.

Specifically, a test suspension containing *Mycobacterium bovis* (ATCC # 35743) was prepared from a frozen suspension of a standardized culture grown in modified Proskauer-Beck medium. The suspension was thawed and mixed with an equal volume of phosphate-buffered gelatin solution in a Teflon-on-glass tissue grinder on ice. The suspension was homogenized for two minutes, then diluted 1:4 in physiological saline solution (PSS) containing 0.1% Tween 80. The suspension was vortexed and held on ice until used in inoculate the test surface.

A neutralizer mixture consisted of 50 ml flasks of Tryptic soy broth containing 1.0% Tween 80, 1.0% lecithin, and 50 μl of concentrated catalase solution (Sigma, C100, 42,300 units/mg).

The CRA environmental Wipe Method which was used is detailed below. An 8×12 inch piece of laminated plastic counter covering was secured to polypropylene dental trays (size B, Zirc Dental) with silicone adhesive. Lids and trays were sterilized by a hydrogen peroxide gas plasma sterilizer. Two ml of test organism suspension was applied to the surface with a sterile 2×2-in cotton-filled gauze sponge. The surface was allowed to dry 20-30 minutes in a biosafety cabinet under laminar flow. Then 3.5 ml of disinfectant (or water) was applied to a sterile gauze sponge, which was used to wipe the inoculated test surface for 10 seconds using about 150-g pressure with overlapping strokes (20 left to right, followed by 20 top to bottom). After 3 minutes, the trays were flooded with 50 ml of neutralizer and scrubbed for 1 minute with a sterile polypropylene brush to remove and suspend organisms. The fluid was collected and serially diluted 1:10 in physiological saline solution (PSS). The number of viable organisms in selected dilution tubes was assayed by membrane filtration. One ml aliquots were plated in duplicate. The membranes were washed with about 100 ml of sterile PSS and removed to *Mycobacteria* 7H11 agar plates. The plates were incubated at 37° C. for about three weeks. The number of colonies on each was counted and log reduction and percent kill values were computed.

As a control, a titer of the test suspension was computed by performing membrane filtration assays of selected 1:10 dilutions of the test suspension in PSS. A neutralizer control was performed by inoculating a mixture of 9 ml of neutralizer and 1 ml of disinfectant with 100 μl of the 1:$10^3$ dilution of the titer containing 1750 CFU. This produced 175 CFU/ml in the tube, which was allowed to stand for 20 minutes prior to dilution and assay of the tubes by membrane filtration using duplicate 1 ml samples.

The results are provided as follows:

TABLE 17a

| Titer | | | |
|---|---|---|---|
| Dilution | 1:1 × $10^3$ | 1:1 × $10^4$ | 1:1 × $10^5$ |
| Number of Colonies | TNC* | TNC | 175 |
| | TNC | TNC | 174 |

*TNC—Too Numerous to Count

TABLE 173b

| Disinfectant solution (Lysol ® Spray) Dilution of *M. bovis*/disinfectant suspension | | |
|---|---|---|
| Dilution | Undiluted | 1:1 × $10^1$ |
| 3 minutes | TNC | 640 |
| | TNC | 486 |

TABLE 17c

| Neutralization control |
|---|
| Undiluted |
| 180 |
| 196 |

TABLE 17d

| Sterility controls | |
|---|---|
| Material | Counts |
| Phosphate buffered gelatin | 0 |
| Neutralizer + catalas | 0 |
| Lysol Spray | 0 |
| Mycobacteria 7H11 Agar | 0 |
| Physiological sterile saline (PSS) + 0.1% Tween 80 | 0 |
| Physiological sterile saline (PSS) | 0 |

Results of the titer showed the initial concentration of *M. bovis* was 1.75×107 CFU per ml in the prepared suspension. Innoculation of the test surface following drying proceduced a challenge exhibited by the water control. The initial concentration of viable bacilli on the test surface (So) was 2.63×$10^5$. Results from these procedures allowed log reduction (LR) and percent kill (PK) values to be calculated using the formulas: 1) LR=−Log(S/So) where S=concentration of viable organisms after a period of exposure to the disinfectant; and So=the initial concentration of viable organisms at time zero; These values are shown in the Table 18 below.

TABLE 18

| Results | | | |
|---|---|---|---|
| Solution | Contact Time | Log Reduction (LR) | Percent Kill (PK) |
| Lysol ® Spray | 3 minutes | 0.97 | 89.3 |

The neutralization control data indicated that each test solution was adequately neutralized. Observed counts were similar to those expected from the titer data.

Example 16

Kill-rate Enhancement Using Silver Alloys

To demonstrate the effectiveness of certain alloys in enhancing the kill rate of *B. Subtilis* bacteria, a composition comprising 0.5% by weight of hydrogen peroxide, 8% by weight ethanol, and the balance of water containing 300 ppm of a colloidal silver was prepared. A similar composition was prepared using identical components except that aqueous solution contained a silver alloy admixture with manganese (approximately 300 ppm silver and about 7 ppm manganese). A kill test was performed resulting in a 0.13 log reduction or a 25.6% kill rate of the *B. subtilis* after 30 seconds using the colloidal silver composition. The kill study was also performed using the colloidal silver-manganese alloy composition, which resulted in a 0.24 log reduction or 42.6% kill after 30 seconds.

Example 17

Degradation of Nitrogen Mustard Gas Using the Disinfectant of Example 5

A surface contaminated with nitrogen mustard gas is at least partially decontaminated composition of Example 5. Specifically, the composition of Example 5 is sprayed on the contaminated surface and is allowed to stand for about 15 minutes. The nitrogen mustard gas is oxidized and degraded into an amine oxide. Similar results can be achieved by oxidizing other chemical agents.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

What is claimed is:

1. A method of decontaminating a surface contaminated with a chemical or biological warfare agent, comprising contacting said surface with a composition, comprising:

a) an aqueous vehicle, including:

i) water, and ii) from 0.001 wt % to 40 wt % of a peroxygen; and b) from 0.001 ppm to 50,000 ppm by weight of a colloidal transition metal or alloy thereof based on the aqueous vehicle content, wherein the transition metal or alloy thereof is an elemental metal selected from the group consisting of ruthenium, rhodium, osmium, iridium, palladium, platinum, copper, gold, silver, alloys thereof, or mixtures thereof; and wherein the composition is substantially free of quaternary ammonium-containing components.

2. A method as in claim 1, wherein the surface being decontaminated is human skin, mucosal tissue, hair, or tissue within the alimentary canal.

3. A method as in claim 1, wherein the surface being decontaminated is a metal, fabric, plastic, composite, glass, wood, or terra firma.

4. A method as in claim 1, wherein said contacting of the contaminated surface can occur by spraying, wiping, pouring, or submersing.

5. A method as in claim 1, wherein the chemical or biological warfare agent is a chemical agent.

6. A method as in claim 5, wherein the chemical agent is selected from the group consisting of Tabun, Sarin, Soman, Cyclohexyl methylphosphonofluoridate, VX, Mustard agent (gas), hydrogen cyanide, arsines, phencyclidine, ricin, abrin, agent 15, or combination thereof.

7. A method as in claim 1, wherein the chemical or biological warfare agent is a biological agent.

8. A method as in claim 7, wherein the biological agent is selected from the group consisting of anthrax, Ebola, Bubonic Plague, Cholera, Tularemia, Brucellosis, Q fever, Machupo, Coccidioides mycosis, Glanders, Melioidosis, Shigella, Rocky Mountain Spotted Fever, Typhus, Psittacosis, Yellow Fever, Japanese B Encephalitis, Rift Valley Fever, Smallpox, or combination thereof.

9. A method as in claim 1, wherein the composition is substantially free of aldehydes.

10. A method as in claim 1, wherein the composition is substantially free of chlorine and bromine-containing components.

11. A method as in claim 1, wherein the composition is substantially free of iodophore-containing components.

12. A method as in claim 1, wherein the composition is substantially free of phenolic-containing components.

13. A method as in claim 1, wherein the composition further comprises an alcohol.

14. A method as in claim 13, wherein the alcohol is present in the composition at from 0.05 wt % to 40 wt %.

15. A method as in claim 13, wherein the alcohol is present in the composition at from 0.05 wt % to 20 wt %.

16. A method as in claim 13, wherein the alcohol is present in the composition at from 0.1 wt % to 10 wt %.

17. A method as in claim 13, wherein the alcohol is a $C_1$-$C_{24}$ alcohol.

18. A method as in claim 17, wherein $C_1$-$C_{24}$ alcohol is selected from the group consisting of methanol, ethanol, propanol, butanol, pentanol, or mixtures thereof.

19. A method as in claim 17, wherein the $C_1$-$C_{24}$ alcohol is a polyhydric alcohol.

20. A method as in claim 19, wherein the polyhydric alcohol is glycerol.

21. A method as in claim 19, wherein the polyhydric alcohol includes two alcohol groups.

22. A method as in claim 19, wherein the polyhydric alcohol includes three alcohol groups.

23. A method as in claim 1, wherein the colloidal transition metal is colloidal silver.

24. A method as in claim 1, wherein the colloidal transition metal or alloy thereof has an average particle size of from 0.001 μm to 1.0 μm.

25. A method as in claim 1, wherein the colloidal transition metal or alloy thereof has an average particle size of from 0.03 μm to 0.5 μm.

26. A method as in claim 1, wherein the transition metal or alloy thereof is present at from 15 ppm to 1500 ppm by weight.

27. A method as in claim 1, wherein the peroxygen is a peracid.

28. A method as in claim 1, wherein the peroxygen is an aliphatic peracid.

29. A method as in claim 1, wherein the peroxygen is an aromatic peracid.

30. A method as in claim 27, wherein the peracid is selected from the group consisting of peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, peroxybenzoic acid, or mixtures thereof.

31. A method as in claim 1, wherein the peroxygen is present at from 0.01 wt % to 30 wt % as part of the aqueous vehicle.

32. A method as in claim 1, wherein the peroxygen is present at from 0.05 wt % to 20 wt % as part of the aqueous vehicle.

33. A method as in claim 1, wherein the peroxygen is present at from 0.1 wt % to 10 wt % as part of the aqueous vehicle.

34. A method as in claim 1, wherein the peroxygen includes a peroxide.

35. A method as in claim 34, wherein the peroxide is hydrogen peroxide.

36. A method as in claim 34, wherein the peroxide is a metal peroxide.

37. A method as in claim 36, wherein the metal peroxide is selected from the group consisting of sodium peroxide, magnesium peroxide, calcium peroxide, barium peroxide, and strontium peroxide, or mixtures thereof.

38. A method as in claim 34, wherein the peroxide is a peroxyhydrate.

39. A method as in claim 34, wherein the peroxide is generated in situ.

40. A method as in claim 34, wherein the peroxide is hydrogen peroxide generated from sodium percarbonate.

41. A method as in claim 1, wherein the peroxygen includes a peracid and a peroxide.

42. A method as in claim 1, wherein the peroxygen is a peracid salt.

43. A method as in claim 42, wherein the peracid salt is selected from the group consisting of permanganates, perborates, perchlorates, peracetates, percitrates, percarbonates, persulphates, or combinations thereof.

* * * * *